(12) United States Patent
Wu et al.

(10) Patent No.: US 11,965,871 B2
(45) Date of Patent: Apr. 23, 2024

(54) METHOD AND SYSTEM FOR INTELLIGENT SOURCE TRACING OF ORGANIC POLLUTION OF WATER BODY

(71) Applicant: NANJING UNIVERSITY, Nanjing (CN)

(72) Inventors: Jichun Wu, Nanjing (CN); Mengwen Liu, Nanjing (CN); Si Wei, Nanjing (CN); Xiaobin Zhu, Nanjing (CN); Nanyang Yu, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 0 days.

(21) Appl. No.: 18/005,565

(22) PCT Filed: Feb. 24, 2022

(86) PCT No.: PCT/CN2022/077587
§ 371 (c)(1),
(2) Date: Mar. 2, 2023

(87) PCT Pub. No.: WO2023/024463
PCT Pub. Date: Mar. 2, 2023

(65) Prior Publication Data
US 2024/0027419 A1     Jan. 25, 2024

(30) Foreign Application Priority Data
Dec. 30, 2021   (CN) .......................... 202111650481.7

(51) Int. Cl.
*G01N 33/18*     (2006.01)
*G01N 30/86*     (2006.01)

(52) U.S. Cl.
CPC ..... *G01N 33/1826* (2013.01); *G01N 30/8637* (2013.01); *G01N 30/8693* (2013.01)

(58) Field of Classification Search
CPC .................. G01N 33/1826; G01N 30/8637
(Continued)

(56) References Cited

U.S. PATENT DOCUMENTS

| 2019/0065674 A1 | 2/2019 | Holland |
| 2022/0157408 A1* | 5/2022 | Vuu .................. G01N 33/0047 |

(Continued)

FOREIGN PATENT DOCUMENTS

| CN | 102661939 A | 9/2012 |
| CN | 107480839 A | 12/2017 |

(Continued)

OTHER PUBLICATIONS

Jianxi Huang et al. "Spatial distribution pattern analysis of groundwater nitrate nitrogen pollution in Shandong intensive farming regions of China using neural network method" Mathematical and Computer Modelling; Dec. 31, 2011; pp. 995-1004.

(Continued)

*Primary Examiner* — Ricky Go (57) ABSTRACT

Disclosed are a method and system for intelligent source tracing of organic pollution of a water body, which belongs to the technical field of environmental analytical chemistry. The method comprises: acquiring organic matter analysis and detection data from water samples of a polluted water body through high performance liquid chromatography-tandem mass spectrometry; performing high-throughput screening on the organic matter in the water samples according to said data to determine pollutants; identifying pollution sources by means of network analysis according to the determined pollutants; and according to the identified pollution sources and the organic pollutants, determining key pollutants and quantifying the pollution contributions thereof by using a machine learning classification model. The present invention can achieve intelligent tracing of the (Continued)

pollution sources and the key pollutants thereof in the case of the pollution sources being unknown, and provide technical support for investigation and control of organic pollution in a water environment.

12 Claims, 4 Drawing Sheets

(58) Field of Classification Search
    USPC .................................................. 702/2
    See application file for complete search history.

(56) References Cited

U.S. PATENT DOCUMENTS

| | | | | |
|---|---|---|---|---|
| 2022/0229036 A1* | 7/2022 | Arnon | ................... | G01N 21/33 |
| 2022/0358266 A1* | 11/2022 | Li | ..................... | G06F 18/23213 |
| 2023/0176027 A1* | 6/2023 | Tzur | ................ | G01N 33/1826 |
| | | | | 356/72 |

FOREIGN PATENT DOCUMENTS

| | | |
|---|---|---|
| CN | 108008048 A | 5/2018 |
| CN | 110004239 A | 7/2019 |
| CN | 110308255 A | 10/2019 |
| CN | 111118128 A | 5/2020 |
| CN | 111161802 A | 5/2020 |
| CN | 112613675 A | 4/2021 |
| CN | 112986497 A | 6/2021 |
| JP | 2019105502 A | 6/2019 |
| WO | 2016122042 A1 | 8/2016 |
| WO | 2021174751 A1 | 9/2021 |

OTHER PUBLICATIONS

Zhang, Huan et al. "Machine learning-based source identification and spatial prediction of heavy metals in soil in a rapid urbanization area, eastern China," Journal of Cleaner Production; Nov. 10, 2020; pp. 1-8; vol. 273.

Notification of the First Office Action dated Jul. 25, 2022 for the Chinese Application No. 202111650481.7.

Tongtong Cao et al. "Identification of Groundwater Contaminant Source Based on Adjoint-state Method," Geological Journal of China Universities; pp. 563-571; vol. 22, Issue 3.

International Search Report and Written Opinion dated Sep. 27, 2022 for International Application No. PCT/CN2022/077587.

\* cited by examiner

METHOD AND SYSTEM FOR INTELLIGENT SOURCE TRACING OF ORGANIC POLLUTION OF WATER BODY

TECHNICAL FIELD

The present invention belongs to the technical field of environmental analytical chemistry, and particularly relates to a method and system for intelligent source tracing of organic pollution of a water body.

BACKGROUND

With the social and economic development, various organic pollutants emerge in endlessly, including but not limited to pesticides and their converted products, drugs and their converted products, surfactants, plasticizers and flame retardants, and other toxic and harmful chemicals in production and use. These organic pollutants continuously enter a water environment and are large in quantity and wide in variety, causing potential ecological and health risks. Therefore, there is a need to pay attention to the organic pollutants in the water environment.

The organic pollutants enter the water environment in a variety of ways, and the existing studies have shown that pollutants flow into surface water by means of sewage discharge from sewage plants, industrial wastewater discharge, surface runoff, underground runoff and other ways, resulting in the problem of wide-sourced and complex organic pollution of the water environment. Therefore, pollutant source tracing of the water environment is a great challenge. The literature research indicates that with regard to the current source tracing of the organic pollutants in the water environment, on the one hand, the source of pollution emission is traced based on the comparison of three-dimensional fluorescence signals between a water body and a pollution source, and on the other hand, a source fingerprint tracing technology is developed based on the characteristic pollutants indicated by the unique mass spectrum signals of the pollution sources themselves. In addition to this, the response of aquatic microbial communities to the change in water quality caused by the source of pollution emission is also used for tracing the pollution source. It is worth noting that currently, these source tracing methods still have obvious shortages: firstly, it is required to set possible pollution sources in advance, and the pollution sources of water bodies are then determined according to the characteristics of the pollution sources; secondly, there is still few identification performed on key pollution factors in the pollution sources and their contributions.

In view of the defects of the existing methods, there is a need to develop a method for tracing sources of a large number of organic pollutants in a water environment without knowing any source of pollution emission.

SUMMARY

Technical Problem: In view of the problems that there are a large number of various organic pollutants in a water environment, which are wide and complex in source, leading to difficulty in source tracing, and existing source tracing technologies rely on knowing pollution sources in advance, the present invention provides an intelligent source tracing method and system for organic pollution of a water body, which can achieve intelligent tracing of pollution sources and key pollutants thereof in the case of the pollution sources being unknown, and provide technical support for investigation and control of organic pollutants in a water environment.

Technical Solution: In a first aspect, the present invention provides a method for intelligent source tracing of organic pollution of a water body, including:
  acquiring organic matter analysis and detection data from a plurality of water samples of a polluted water body from upstream to downstream through high performance liquid chromatography-tandem mass spectrometry;
  performing high-throughput screening on the organic matter in the water samples according to the analysis and detection data to determine pollutants in the water body;
  identifying pollution sources by means of network analysis according to the determined pollutants; and
  according to the identified pollution sources and the organic pollutants in the receiving water body at the pollution sources, determining key pollutants in the pollution sources and quantifying the pollution contributions of the key pollutants by using a machine learning classification model.

Further, performing high-throughput screening on the organic matter in the water samples according to the analysis and detection data to determine pollutants in the water body includes:
  importing data files obtained by means of analysis and detection into analysis software, such as MS-DIAL, PeakView, or Compound Discover, to perform peak extraction and alignment, using a public large mass spectrometry database to perform the high-throughput screening on the organic matter in the water samples, manually checking the matching of secondary spectra to remove false positives, and determining the pollutants in the water body according to the matter classification information provided by PubChem.

Further, identifying pollution sources by means of network analysis according to the determined pollutants includes:
  calculating the correlation of the peak areas of the organic pollutants, constructing a correlation-based pollutant network according to the correlation, and performing group classification on the pollutant network;
  according to the pollutant groups, drawing change curves of the peak areas of the pollutants in the groups and change curves of mean peak areas of the pollutants in the groups; and
  according to the sites where the change curves of the mean peak areas of the pollutants in the large groups sharply increase from upstream to downstream, determining location intervals of potential pollution sources, and meanwhile, considering the consistency of the peak areas of the pollutants in the groups at the sites, determining the pollution sources according to actual geographic information.

Further, calculating the correlation of the peak areas of the organic pollutants, constructing a correlation-based pollutant network according to the correlation, and performing group classification on the pollutant network, includes:
  calculating the correlation of the peak areas of the organic pollutants in the water samples of the receiving water body from upstream to downstream, retaining the correlation relationship with the significance ($p<0.05$, where the p value is a positive value), taking the correlation relationship as an edge and the pollutants as nodes, inputting them into the network analysis software, such as Gephi or Cytoscape, to construct the correlation-based pollutant network, and performing modular analysis to obtain a group classification result of the pollutant network.

Further, according to the categories of the pollutant groups, drawing change curves of the peak areas of the pollutants in the groups and change curves of mean peak areas of the pollutants in the groups includes:

standardizing the peak areas of the pollutants in the water samples from upstream to downstream, and drawing change curve graphs of the peak areas of the pollutants in the groups according to the categories of the pollutant groups;

according to the categories of the pollutant groups, calculating mean values of the peak areas of the pollutants at each site to obtain the change curves of the mean peak areas of the pollutants in the groups.

Further, the machine learning classification model is a random forest model.

Further, according to the identified pollution sources and the organic pollutants in the receiving water body at the pollution source, determining key pollutants in the pollution sources and quantifying the pollution contributions of the key pollutants by using a machine learning classification model, includes:

determining the organic pollutants in the water samples of the receiving water body into which the determined pollution sources flow, selecting the organic pollutants existing in both the pollution sources and the receiving water body, and taking the peak areas of the organic pollutants at each site of the receiving water body as inputs;

constructing the random forest classification model, and taking the samples of the receiving water body as criteria for binary classification relative to the upstream or the downstream of the pollution sources;

training the random forest classification model; and outputting indexes indicating the importance of variables, and determining the key pollutants and the pollution contributions of the key pollutants according to values of the importance indexes.

Further, outputting indexes indicating the importance of variables, and determining the key pollutants and the pollution contributions of the key pollutants according to values of the importance indexes, includes:

if the values of mean decrease accuracy of the variables are greater than set thresholds thereof, regarding the key pollutants as potential pollution contribution factors, and judging the relationship between the maximum values of the peak areas of the factors in downstream samples of the receiving water body closest to the pollution sources and the maximum values thereof in all upstream samples of the receiving water body; and if the peak areas of the potential pollution contribution factors in the downstream samples closest to the pollution sources are greater than those in the upstream samples, i.e., the relative abundances thereof increase, regarding the factors as the key pollutants in the pollution source, and quantifying the pollution contributions of the key pollutants on the basis of the values of mean decrease accuracy of these key pollutants.

Further, acquiring organic matter analysis and detection data from a plurality of water samples of a polluted water body from upstream to downstream through high performance liquid chromatography-tandem mass spectrometry includes:

collecting the water samples of the polluted water body from upstream to downstream;

treating the water samples to extract and enrich the organic matter in the water samples as comprehensively as possible to obtain liquids to be detected; and analyzing and detecting the organic matter of the samples by using high performance liquid chromatography-tandem mass spectrometry.

In a second aspect, the present invention provides a system for intelligent source tracing of organic pollution of a water body, which uses any one of the methods for intelligent source tracing of organic pollution of a water body provided by the present invention. The system includes:

a data acquisition unit for acquiring organic matter analysis and detection data from a plurality of water samples of a polluted water body from upstream to downstream through high performance liquid chromatography-tandem mass spectrometry;

a pollutant determination unit for performing high-throughput screening on the organic matter in the water samples according to the analysis and detection data to determine pollutants in the water body;

a pollution source identification unit for identifying pollution sources by means of network analysis according to the determined pollutants; and a pollution source evaluation unit for determining, according to the identified pollution sources and the organic pollutants in the receiving water body at the pollution sources, key pollutants in the pollution sources and quantifying the pollution contributions of the key pollutants by using a machine learning classification model.

Beneficial Effects: Compared with the prior art, the present invention has the advantages as follows:

The present invention constructs a correlation network chart of organic pollutants using the peak areas of the pollutants in the receiving water body (i.e., the correlation relationship of relative abundances), so that the pollutants similar in the variation trends of relative abundances in the receiving water body can be visually clustered, and the groups with similar distribution trends can be efficiently and quickly found in a large number of pollutants, and the groups with a large number of pollutants can also be quickly focused, the geographical location intervals where the pollution sources are located can be effectively traced according to the variation trends of the mean relative abundances of the groups, and the pollution sources can be identified according to geographical information. The water samples of the receiving water body are classified relative to the upstream and downstream of the pollution sources, and the machine learning classification model is constructed to find the potential pollution contribution factors, so that according to the relative abundances of the samples in the upstream and downstream, the key pollution contribution factors to the receiving water body can be found in a large number of pollutants by means of screening, the key pollutants can be effectively identified on the basis of identifying the pollution source, and the pollution contribution of the pollutants can also be quantified according to the values of important indexes.

The high-throughput screening, the network analysis and the machine learning technology are comprehensive used in the whole process, so that the intelligent tracing of the pollution sources and the key pollutants thereof can be achieved in the case of the pollution sources being unknown, the technical support can be provided for investigation and control of organic pollutants in the water environment.

DETAILED DESCRIPTION OF THE INVENTION

The present invention will be further described below with reference to embodiments and accompanying drawings of the description.

Figure 1:
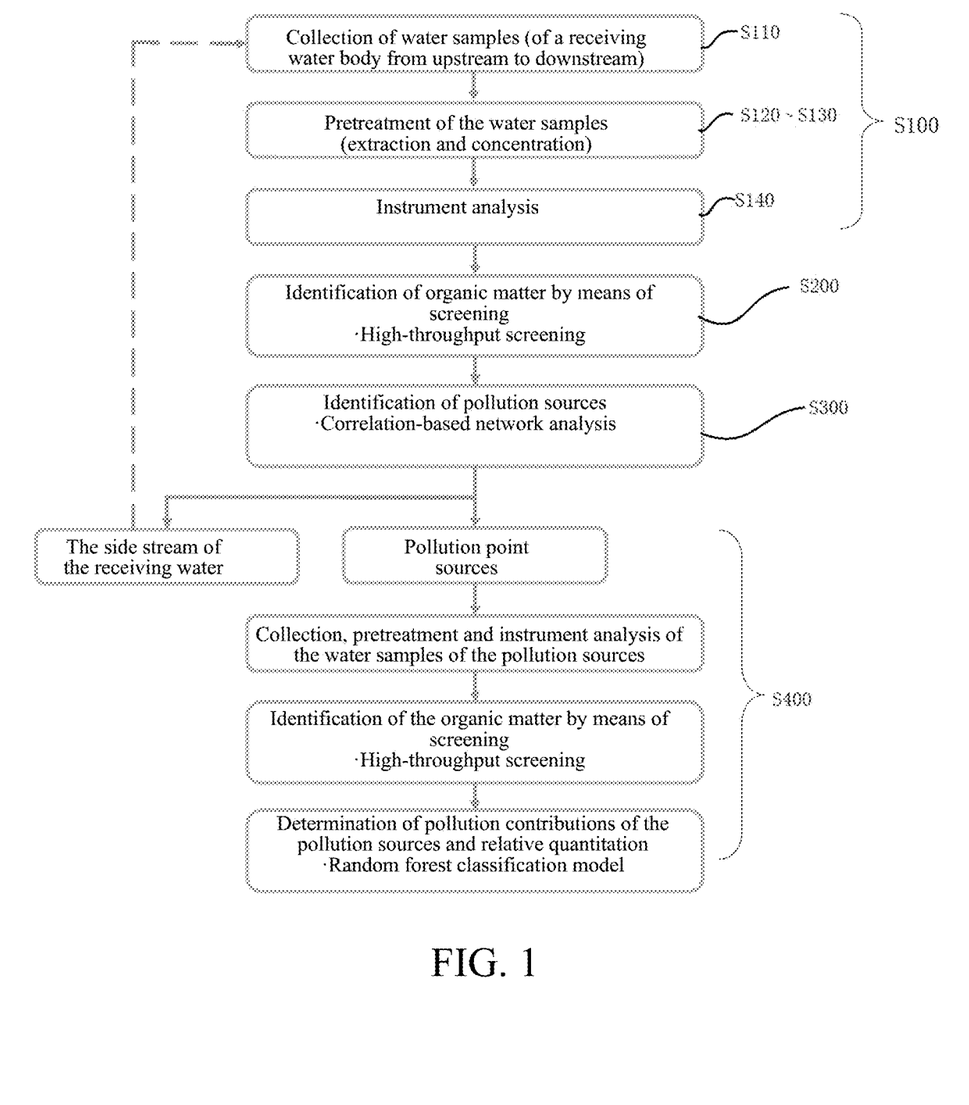
FIG. 1 is a flow chart of a method for intelligent source tracing of organic pollution of a water body according to an embodiment of the present invention.

In a first aspect, the present invention provides a method for intelligent source tracing of organic pollution of a water body. FIG. 1 illustrates a flow chart of the method for intelligent source tracing of organic pollution of the water body in an embodiment of the present invention, and in conjunction with FIG. 1, the method in the embodiment includes:

Step S100: acquiring organic matter analysis and detection data from a plurality of water samples of a polluted water body from upstream to downstream through high performance liquid chromatography-tandem mass spectrometry. In the embodiment of the present invention, in conjunction with specific examples, the step may be executed according to sub-steps S110-S140:

Step S110: collection of the water samples. River water samples are collected from 11 sites from upstream to downstream.

Step S120: extraction of the organic matter from the river water samples. 1 L of river water samples are filtered using 1 μm glass fiber filter membrane, the organic matter in the samples is then enriched by means of a solid phase extraction (SPE) method, the water samples sequentially flow through Oasis MAX, MCX and HLB solid phase extraction columns, and the flow rates through the columns are controlled to be about 3 mL/min. Activation is needed before the columns are used: with regard to the MAX columns, 10 ml of 2% formic acid-methanol solution, 10 ml of methanol and 10 ml of Fisher water are added in sequence; with regard to the MCX columns, 10 ml of 5% aqueous ammonia-methanol solution, 10 ml of methanol and 10 ml Fisher water are added in sequence; with regard to the HLB columns, 10 ml of methanol and 10 ml of Fisher water are added in sequence. After completion of water sample filtering, the extraction columns are first subjected to centrifugal dehydration (3,000 rpm, 5 min) by using a centrifuge and are then eluted: with regard to the MAX columns, 12 ml of 2% formic acid-methanol solution is added; with regard to the MCX columns, 12 ml of 5% aqueous ammonia-methanol solution is added; with regard to the HLB columns, 12 ml of methanol is added. The eluates of the same water samples are mixed to obtain final extraction eluates.

Step S130: concentration and volume quantitation. The eluates are evaporated to near dryness by nitrogen blow, the volumes are quantized to 1 ml with methanol, and supernatants are then obtained by means of centrifugation and stored to sample vials.

Step S140: instrument analysis. The samples are subjected to organic matter analysis and detection by means of a high performance liquid chromatography-hybrid quadrupole orbitrap mass spectrometer under the following instrument conditions:

High performance liquid chromatograph: Thermo UltiMate 3000;
Chromatographic column: Acquity UPLC BEH C18 column (2.1×150 mm, 1.7 μm);
Column temperature: 40° C.;
Flow rate: 0.3 ml/min;
Mobile phases: 2 mM ammonium acetate water solution (A phase), and methanol (B phase);
Elution gradient:

| Time (min) | A (%) | B (%) |
| --- | --- | --- |
| 0.00 | 90.0 | 10.0 |
| 1.00 | 90.0 | 10.0 |
| 36.00 | 0.0 | 100.0 |
| 50.00 | 0.0 | 100.0 |
| 50.10 | 90.0 | 10.0 |
| 55.00 | 90.0 | 10.0 |

Mass spectrometer: Q Exactive Focus, Thermo Scientific;
Ion source: electrospray;
Ion modes: positive ion mode and negative ion mode;
Primary (MS) full scan range: 80-1,000 m/z;
Primary (MS) resolution: 70,000;
Secondary (MS/MS) resolution: 17,500;
Spray voltages: 3,500 V (positive ion mode); 2,500V (negative ion mode);
Collision energy: 35±15 eV (positive ion mode); −35±15 eV (negative ion mode);

Step S200: performing high-throughput screening on the organic matter in the water samples according to the analysis and detection data to determine pollutants in the water body. Specifically, in the embodiment of the present invention, the data files obtained in step S100 are imported into the MS-DIAL software to perform peak extraction and alignment, high-throughput screening is performed on the organic matter in water samples using a public large mass spectrometry database, the matching of secondary spectra are manually checked to remove false positives, and the pollutants therein are determined according to the matter classification information provided by PubChem. In other embodiments of the present invention, the step may also be performed using other software such as PeakView, or compound Discover, and other large public mass spectrometry databases such as MS-DIAL, NIST, MassBank or GNPS mass spectrometry database.

The parameters are set as follows: peak rise response: ≥30,000; the retention time error of alignment: ≤0.2 min; the error of alignment quality: ≤0.01 Da; the error of screening quality: primary screening ≤0.01 Da, and secondary screening ≤0.002 Da.

The criteria for removing false positives by manual checking are as follows: if there is only one piece of fragment ion information in a secondary spectrum in the database, the matter with no fragment ion unmatched shall be removed; if there are two or more pieces of fragment ion information in the secondary spectrum in the database, the matter with less than two fragment ions matched shall be removed; and if there is no fragment ion information in the secondary spectrum in the database, the matter shall be removed.

Finally, 132 organic pollutants in the river are identified by means of screening.

Figure 2:
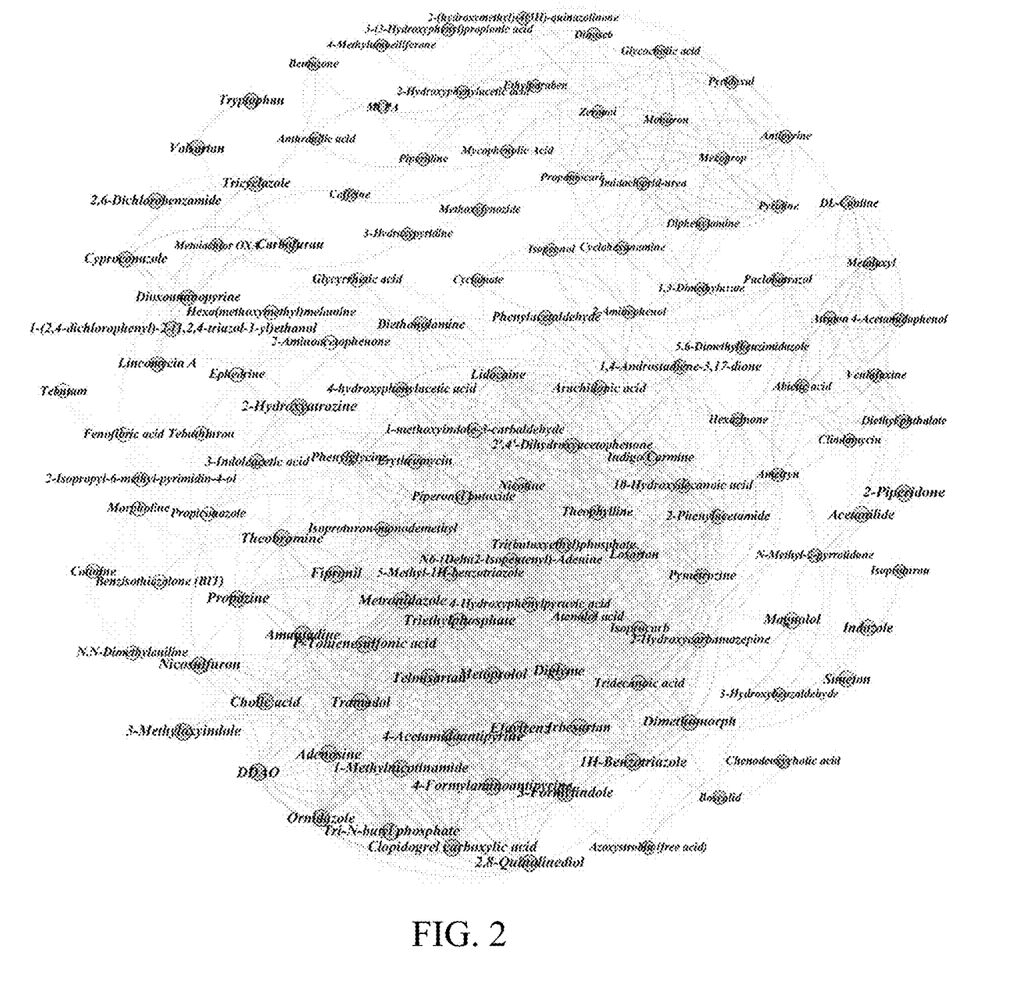
FIG. 2 is a chart illustrating a correlation-based pollutant network obtained by means of network analysis according to an embodiment of the present invention.
Figure 3:
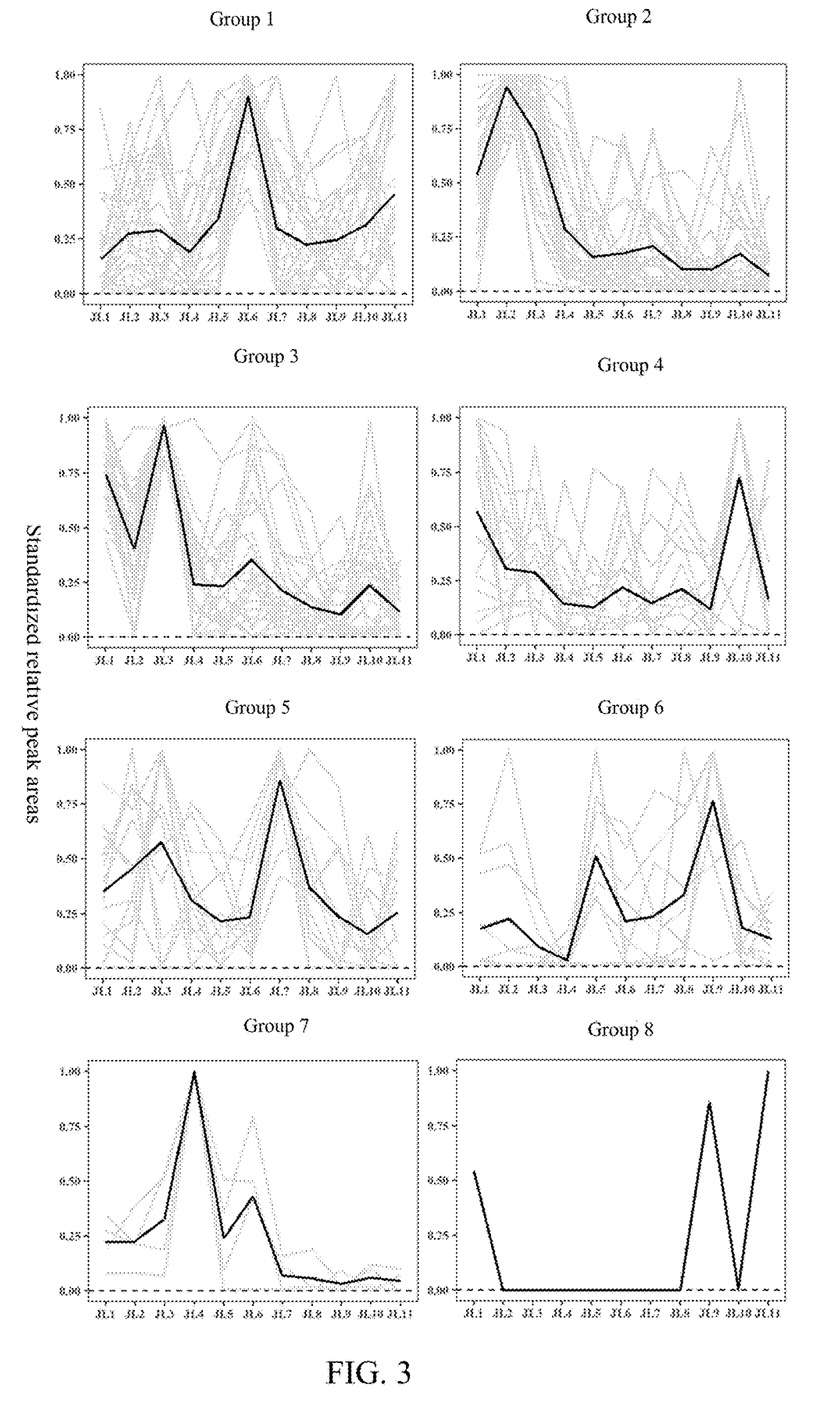
FIG. 3 shows change curve graphs of peak areas of pollutants of 8 groups obtained by means of network analysis according to an embodiment of the invention.

Step S300: identifying pollution sources by means of network analysis according to the determined pollutants. Specifically, the step includes:

Step S310: calculating the correlation of the peak areas of the organic pollutants, constructing a correlation-based pollutant network according to the correlation, and performing group classification on the pollutant network. In the embodiment of the present invention, the Pearson correlation of the peak areas of the organic pollutants in the water samples of the receiving water body from upstream to downstream is calculated, the correlation relationship with the significance ($p<0.05$, where the p value is a positive value) is retained, the correlation relationship is taken as an edge and the pollutants as nodes, they are input into the Gephi software to construct the correlation-based pollutant network, and modular analysis is performed to obtain a group classification result of the pollutant network. In the example provided by the present invention, the correlation-based pollutant network is shown in FIG. 2, and the pollutant network is classified into 8 different groups, as shown in FIG. 3. In other embodiments of the present invention, Cytoscape software may also be used to build a correlation-based pollutant network.

Step S320: according to the pollutant groups, drawing change curves of the peak areas of the pollutants in the groups and change curves of mean peak areas of the pollutants in the groups; specifically, standardizing the peak areas of the pollutants in the water samples from upstream to downstream, and drawing change curve graphs of the peak areas of the pollutants in the groups according to the categories of the pollutant groups; on this basis, calculating mean values of the peak areas of the pollutants at each site to obtain the change curves of the mean peak areas of the pollutants in the groups. In the example provided, the change curves are shown in FIG. 3.

Step S330: according to the sites where the change curves of the mean peak areas of the pollutants in the large groups sharply increase from upstream to downstream, determining location intervals of potential pollution sources, and meanwhile, considering the consistency of the peak areas of the pollutants in the groups at the sites, determining the pollution sources according to actual geographic information.

If the traced side streams of the receiving water body are the pollution sources, steps S100-S300 should be repeated until specific pollution point sources are identified.

Specifically, in conjunction with FIG. 3, the black curves are the change curves of the mean peak areas of the pollutants. The gray curves are the change curves of the peak areas of the pollutants. When determining the pollution sources, it can be seen that where the change curves of the mean peak areas of the pollutants increase sharply, the change curves of the peak areas of most pollutants also increase sharply, and the pollution sources can be determined according to the actual geographic information. In the example provided, the location intervals of two potential pollution sources are determined according to the sites where the curves of the pollutants in the first three large groups increase sharply from upstream to downstream, and the consistency of sharp increases of the peak areas of pollutants in the three groups at the two sites are considered, and it is determined according to the actual geographic information that a nearby sewage treatment plant and a side stream thereof are the pollution sources.

Step S400: according to the identified pollution sources and the organic pollutants in the receiving water body at the pollution sources, determining key pollutants in the pollution sources and quantifying the pollution contributions of the key pollutants by using a machine learning classification model.

In an embodiment of the present invention, the machine learning classification model used is a random forest model. Of course, in other embodiments, other classification models may be used, such as a decision tree, or a support vector machine. The specific description is given herein by combining with the random forest model, and specifically, it may be performed according to steps S410-S440.

Step S410: determining the organic pollutants in the water samples of the receiving water body into which the determined pollution sources flow, selecting the organic pollutants existing in both the pollution sources and the receiving water body, and taking the peak areas of the organic pollutants at each site of the receiving water body as inputs. When the organic pollutants of the pollution sources flowing into the receiving water body are determined, it is possible to perform detection according to method in steps S110-S140, and then identify the organic pollutants thereof by means of screening according to method in step S200. In the example provided, 76 organic pollutants are finally identified from the wastewater samples of the sewage treatment plant by means of screening. A total of 71 organic pollutants existing in both the wastewater and the river are selected, and their peak areas of the organic pollutants at the sites of the river are taken as inputs.

Step S420: constructing the random forest classification model, and taking the samples of the receiving water body as criteria for binary classification relative to the upstream or the downstream of the pollution source.

In the example provided, the random forest classification model is constructed using an R language, and the river samples are classified into 8 upstream samples and 3 downstream samples relative to the pollution sources.

Step S430: training the random forest classification model. In the example provided, it is determined by cyclically calculating the out-of-bag error rate (OOB) that the optimum value of a model parameter mtry is 16 and the classification error rate of a confusion matrix evaluation model is 0%.

Figure 4:
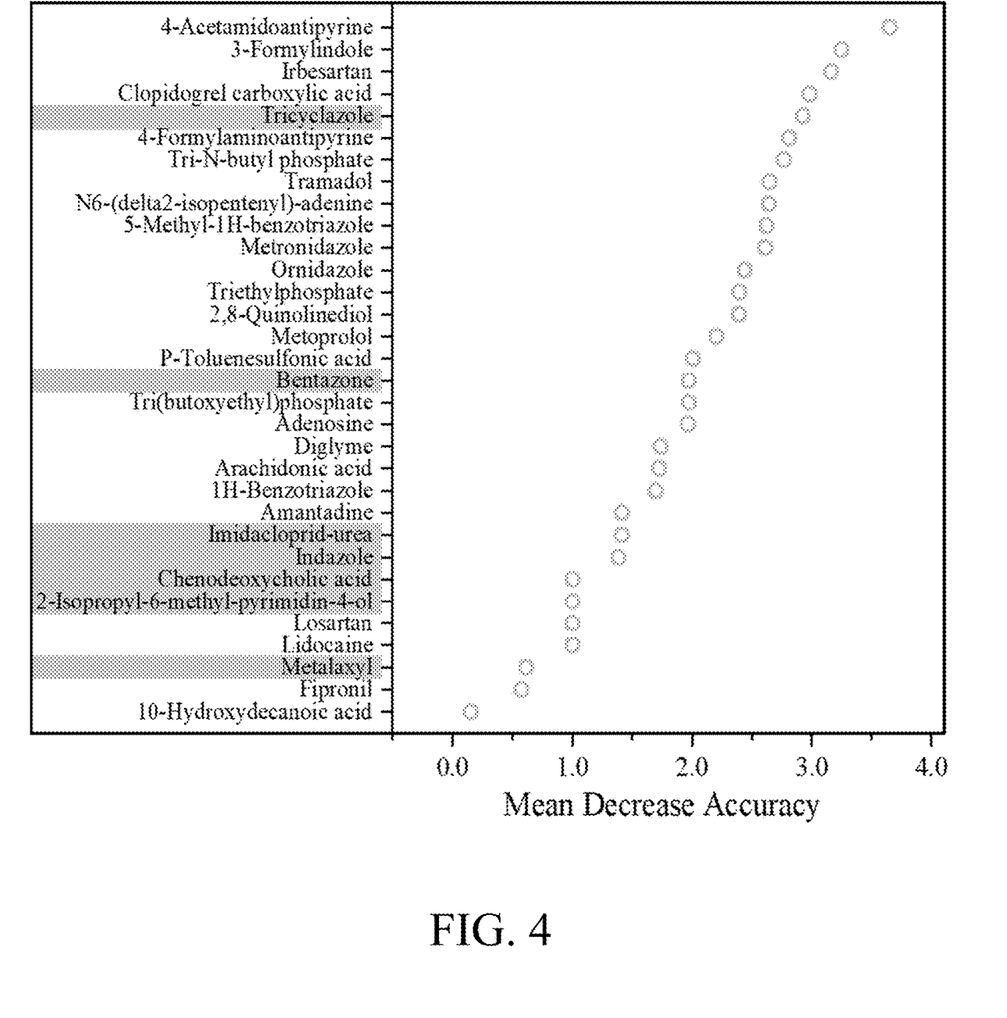
FIG. 4 is a value graph illustrating importance indexes of pollutants output by a machine learning model according to an embodiment of the invention.

Step S440: outputting indexes indicating the importance of variables, and determining the key pollutants and the pollution contributions of the key pollutants according to values of the importance indexes. In the example provided, the indexes used are the values of mean decrease accuracy. With regard to 32 pollutants with their values of mean decrease accuracy greater than 0 (a set threshold value), it is determined whether their peak areas in the downstream river samples closest to the pollution sources are greater than the maximum values in all the upstream river samples, and it is finally found that 25 pollutants are key pollution contribution factors in the pollution point sources of the sewage treatment plant, and their pollution contributions are quantified based on their values of mean decrease accuracy, as shown in FIG. 4.

In a second aspect, the present invention provides a system for intelligent source tracing of organic pollution of a water body, which can perform source tracing by using the method for intelligent source tracing of organic pollution of a water body described above. The system includes:

a data acquisition unit for acquiring organic matter analysis and detection data from a plurality of water samples of a polluted water body from upstream to downstream through high performance liquid chromatography-tandem mass spectrometry;

a pollutant determination unit for performing high-throughput screening on the organic matter in the water samples according to the analysis and detection data to determine pollutants in the water body;

a pollution source identification unit for identifying pollution sources by means of network analysis according to the determined pollutants; and a pollution source evaluation unit for determining, according to the identified pollution sources and the organic pollutants in the receiving water body at the pollution sources, key pollutants in the pollution sources and quantifying the pollution contributions of the key pollutants by using a machine learning classification model.

The units described above implement the functions corresponding to the respective steps in the method provided by the present invention, which will not be described in detail herein.

The above example is only a preferred embodiment of the present invention, it should noted that for those of ordinary skill in the art, several improvements and equivalent substitutions may also be made without departing from the principle of the present invention, and after these improvements and equivalent substitutions are made on the claims of the present invention, their technical solutions shall fall within the scope of the present invention as defined by the appended claims.

The invention claimed is:

1. A method for intelligent source tracing of organic pollution of a water body, comprising:

acquiring organic matter analysis and detection data from a plurality of water samples of a polluted water body from upstream to downstream through high performance liquid chromatography-tandem mass spectrometry;

performing high-throughput screening on the organic matter in the water samples according to the analysis and detection data to determine pollutants in the water body;

identifying pollution sources by means of network analysis according to the determined pollutants; and according to the identified pollution sources and the organic pollutants in the receiving water body at the pollution sources, determining key pollutants in the pollution sources and quantifying the pollution contributions of the key pollutants by using a machine learning classification model;

wherein identifying pollution sources by means of network analysis according to the determined pollutants comprises:

calculating the correlation of the peak areas of the organic pollutants, constructing a correlation-based pollutant network according to the correlation, and performing group classification on the pollutant network;

according to the pollutant groups, drawing change curves of the peak areas of the pollutants in the groups and change curves of mean peak areas of the pollutants in the groups; and according to the sites where the change curves of the mean peak areas of the pollutants in the large groups sharply increase from upstream to downstream, determining location intervals of potential pollution sources, and meanwhile, considering the consistency of the peak areas of the pollutants in the groups at the sites, determining the pollution sources according to actual geographic information;

wherein calculating the correlation of the peak areas of the organic pollutants, constructing a correlation-based pollutant network according to the correlation, and performing group classification on the pollutant network, comprises:

calculating the correlation of the peak areas of the organic pollutants in the water samples of the receiving water body from upstream to downstream, taking the correlation relationship as an edge and the pollutants as nodes, inputting them into the network analysis software, such as Gephi or Cytoscape to construct the correlation-based pollutant network, and performing modular analysis to obtain a group classification result of the pollutant network;

wherein according to the categories of the pollutant groups, drawing change curves of the peak areas of the pollutants in the groups and change curves of mean peak areas of the pollutants in the groups comprises:

standardizing the peak areas of the pollutants in the water samples from upstream to downstream, and drawing change curve graphs of the peak areas of the pollutants in the groups according to the categories of the pollutant groups;

according to the categories of the pollutant groups, calculating mean values of the peak areas of the pollutants at each site to obtain the change curves of the mean peak areas of the pollutants in the groups.

2. The method of claim 1, wherein according to the analysis and detection data, performing high-throughput screening on the organic matter in the water samples to determine pollutants in the water body comprises:

importing data files obtained by means of analysis and detection into analysis software to perform peak extraction and alignment, using a public large mass spectrometry database to perform the high-throughput screening on the organic matter in the water samples, manually checking the matching of secondary spectra to remove false positives, and determining the pollutants in the water body according to the matter classification information provided by PubChem.

3. The method of claim 2, wherein the machine learning classification model is a random forest model.

4. The method of claim 1, the calculating the correlation of the peak areas of the organic pollutants in the water samples of the receiving water body from upstream to downstream, retaining the correlation relationship with the significance $p<0.05$, where the p value is a positive value.

5. A system for intelligent source tracing of organic pollution of a water body, which uses the method for intelligent source tracing of organic pollution of a water body described in of claim 4, the system comprising:

a data acquisition unit for acquiring organic matter analysis and detection data from a plurality of water samples of a polluted water body from upstream to downstream through high performance liquid chromatography-tandem mass spectrometry;

a pollutant determination unit for performing high-throughput screening on the organic matter in the water samples according to the analysis and detection data to determine pollutants in the water body;

a pollution source identification unit for identifying pollution sources by means of network analysis according to the determined pollutants; and a pollution source evaluation unit for determining, according to the identified pollution sources and the organic pollutants in the receiving water body at the pollution sources, key pollutants in the pollution sources and quantifying the pollution contributions of the key pollutants by using a machine learning classification model.

6. The method of claim 4, wherein the machine learning classification model is a random forest model.

7. The method of claim 1, wherein the machine learning classification model is a random forest model.

8. The method of claim 7, wherein according to the identified pollution sources and the organic pollutants in the receiving water body at the pollution sources, determining key pollutants in the pollution sources and quantifying the pollution contributions of the key pollutants by using a machine learning classification model comprises:
   determining the organic pollutants in the water samples of the receiving water body into which the determined pollution sources flow, selecting the organic pollutants existing in both the pollution sources and the receiving water body, and taking the peak areas of the organic pollutants at each site of the receiving water body as inputs;
   constructing the random forest classification model, and taking the samples of the receiving water body as criteria for binary classification relative to the upstream or the downstream of the pollution sources;
   training the random forest classification model; and
   outputting indexes indicating the importance of variables, and determining the key pollutants and the pollution contributions of the key pollutants according to values of the indexes.

9. The method of claim 8, wherein outputting indexes indicating the importance of variables, and determining the key pollutants and the pollution contributions of the key pollutants according to values of the importance indexes, comprises:
   if the values of the importance indexes are greater than variables of set thresholds, regarding the pollutants as potential pollution contribution factors, and judging the relationship between the maximum values of the peak areas of the factors in downstream samples and upstream samples of the receiving water body relative to the pollution sources; and
   if the peak areas of the potential pollution contribution factors in the downstream samples are greater than the peak areas in the upstream samples, regarding the factors as the key pollutants in the pollution sources, and quantifying the pollution contributions of the key pollutants on the basis of the values of the importance indexes of these key pollutants.

10. The method of claim 9, wherein acquiring organic matter analysis and detection data from a plurality of water samples of a polluted water body from upstream to downstream through high performance liquid chromatography-tandem mass spectrometry comprises:
   collecting the water samples of the polluted water body from upstream to downstream;
   treating the water samples to extract and enrich the organic matter in the water samples as comprehensively as possible to obtain liquids to be detected; and
   analyzing and detecting the organic matter of the samples by using high performance liquid chromatography-tandem mass spectrometry.

11. A system for intelligent source tracing of organic pollution of a water body, which uses the method for intelligent source tracing of organic pollution of a water body described in of claim 1, the system comprising:
   a data acquisition unit for acquiring organic matter analysis and detection data from a plurality of water samples of a polluted water body from upstream to downstream through high performance liquid chromatography-tandem mass spectrometry;
   a pollutant determination unit for performing high-throughput screening on the organic matter in the water samples according to the analysis and detection data to determine pollutants in the water body;
   a pollution source identification unit for identifying pollution sources by means of network analysis according to the determined pollutants; and
   a pollution source evaluation unit for determining, according to the identified pollution sources and the organic pollutants in the receiving water body at the pollution sources, key pollutants in the pollution sources and quantifying the pollution contributions of the key pollutants by using a machine learning classification model.

12. A method for intelligent source tracing of organic pollution of a water body, comprising:
   acquiring organic matter analysis and detection data from a plurality of water samples of a polluted water body from upstream to downstream through liquid chromatography-mass spectrometry;
   performing screening on the organic matter in the water samples according to the analysis and detection data to determine pollutants in the water body;
   identifying pollution sources by means of network analysis according to the determined pollutants; and
   according to the identified pollution sources and the organic pollutants in the receiving water body at the pollution sources, determining key pollutants in the pollution sources and quantifying the pollution contributions of the key pollutants by using a machine learning classification model;
   wherein identifying pollution sources by means of network analysis according to the determined pollutants comprises:
   calculating the correlation of the peak areas of the organic pollutants, constructing a correlation-based pollutant network according to the correlation, and performing group classification on the pollutant network;
   according to the pollutant groups, drawing change curves of the peak areas of the pollutants in the groups and change curves of mean peak areas of the pollutants in the groups; and
   according to the sites where the change curves of the mean peak areas of the pollutants in the large groups sharply increase from upstream to downstream, determining location intervals of potential pollution sources, and meanwhile, considering the consistency of the peak areas of the pollutants in the groups at the sites, determining the pollution sources according to actual geographic information;
   wherein calculating the correlation of the peak areas of the organic pollutants, constructing a correlation-based pollutant network according to the correlation, and performing group classification on the pollutant network, comprises:
   calculating the correlation of the peak areas of the organic pollutants in the water samples of the receiving water body from upstream to downstream, taking the correlation relationship as an edge and the pollutants as nodes, inputting them into the network analysis software, such as Gephi or Cytoscape to construct the correlation-based pollutant network, and performing modular analysis to obtain a group classification result of the pollutant network;

wherein according to the categories of the pollutant groups, drawing change curves of the peak areas of the pollutants in the groups and change curves of mean peak areas of the pollutants in the groups comprises:

standardizing the peak areas of the pollutants in the water samples from upstream to downstream, and drawing change curve graphs of the peak areas of the pollutants in the groups according to the categories of the pollutant groups; and according to the categories of the pollutant groups, calculating mean values of the peak areas of the pollutants at each site to obtain the change curves of the mean peak areas of the pollutants in the groups.

* * * * *